United States Patent [19]

Kaminski

[11] Patent Number: 5,547,969
[45] Date of Patent: *Aug. 20, 1996

[54] METHOD FOR THE TREATMENT OF BRADYPHRENIA IN PARKINSON'S DISEASE PATIENTS

[75] Inventor: Ram Kaminski, Riverdale, N.Y.

[73] Assignee: Mount Sinai School of Medicine of the City University of New York, N.Y.

[ * ] Notice: The term of this patent shall not extend beyond the expiration date of Pat. No. 5,5,352,688.

[21] Appl. No.: 314,414

[22] Filed: Sep. 28, 1994

Related U.S. Application Data

[60] Division of Ser. No. 954,258, Sep. 30, 1992, Pat. No. 5,352,688, which is a continuation-in-part of Ser. No. 743,254, Aug. 9, 1991, Pat. No. 5,177,081, which is a division of Ser. No. 655,759, Feb. 14, 1991, Pat. No. 5,070,101.

[51] Int. Cl.$^6$ .................... A61K 31/425; A61K 31/34
[52] U.S. Cl. ................................. 514/370; 514/471
[58] Field of Search ...................... 514/370, 471

[56] References Cited

U.S. PATENT DOCUMENTS

| | | | |
|---|---|---|---|
| 4,757,060 | 4/1986 | Lukacsko et al. | 514/160 |
| 4,806,548 | 2/1989 | Ivanova et al. | 514/310 |
| 5,070,101 | 12/1991 | Kaminski | 514/399 |
| 5,177,081 | 1/1993 | Kaminski | 514/279 |
| 5,352,688 | 10/1994 | Kaminski | 514/357 |

OTHER PUBLICATIONS

Cahill et al, *Chemical Abstracts*, vol. 104, No. 19, May 1986, Abstract 166327c, p. 481.
Kaminski et al., 1990, The Lancet, 335:1351–1352.
Alan J. Gelenberg, M.D., 1990, Biological Therapies in Psychiatry Newsletter vol. 13, No. 11.
Drug Information for the Health Care Professional, 1990, USP DI 1990 10th Anniversary Edition, pp. 1495–1505.
Joseph R. Bianchine, 1985, MacMillan Publishing Company, Goodman and Gilman's The Pharmacological Basis of Therapeutics, Seventh Edition, 21:472–486.
Growdon et al., 1990, Advances in Neurology 53:365–37, Parkinson's Disease: Anatomy, Pathology, and Therapy.
Danilczyk et al., 1990, Advances in Neurology 53:405–410, Parkinson's Disease: Anatomy, Pathology and Therapy.
Calne et al., 1990, Advances in Neurology, Parkinson's Disease: Anatomy, Pathology and Therapy, 53:355–360.
Y. Agid et al., 1990, Advances in Neurology 53:83–100, Parkinson's Disease: Anatomy, Pathology and Therapy.
J. L. Cummings, M.D., 1992, Am. J. Psychiatry 149:4, 443–454.
M. Garbarg et al., 1983, The Lancet, 74–75.
M. H. Coelho et al., 1991, Molecular and Chemical Neuropathology 14:77–85.
J. Poirier et al., 1987, The Lancet p. 386.
S. Nakamura and S. Vincent, 1986, Neuroscience Letters 65:321–325.
Cumming et al., 1989, European Journal of Pharmacology 166:299–301.
U. Knigge and J. Warberg, 1991, Acta Endocrinologica (Copenh) 124:609–619.
Cumming et al., 1990, European Journal of Pharmacology 184:299–301.
Oishi et al., 1990, European Journal of Pharmacology 184:135–142.
Cumming et al., 1991, SYNAPSE 8 pp. 144–151.
S. Chiavegatto et al., 1991, Pharmacology Biochemistry & Behavior 140:191–193.
Matzen et al., 1990, Neuroendocrinology 52:175–180.
Sakai et al., 1991, Life Sciences 48:2397–2404.
Onodera er al., 1991, Birkhauser Verlag, Basel, Agents and Actions 33:143–146.
U. P. Knigge, 1990, Danish Medical Bulletin vol. 37, No. 2:109–124.
A. Eisen and D. Calne, 1992, Can. J. Neurol. Sci 19:117–120.
Dooneief, M.D. et al., 1992, Arch Neurol, 49:305–307.
M. H. Sharpe, 1992, Neuropsychologia vol. 30, No. 1:101–106.
Berkow et al., 1981, "The Merck Manual of Diagnosis and Therapy", 14th Edition, published by Merck, Sharp & Sohne Research Laboratories, pp. 1359–1362 and 2336–2337.

*Primary Examiner*—Marianne M. Cintins
*Assistant Examiner*—William R. A. Jarvis
*Attorney, Agent, or Firm*—Brumbaugh, Graves, Donohue & Raymond

[57] ABSTRACT

The neuropsychiatric symptom of bradyphrenia in a Parkinson's Disease patient may be ameliorated by treating the patient with a histamine $H_2$-antagonist that passes the blood brain barrier. Suitable $H_2$-antagonists include famotidine and ranitidine. The $H_2$-antagonists may be co-administered with other compounds such as histamine $H_1$-antagonists which are known to be useful in the treatment of Parkinson's Disease, and can be formulated with such other compounds into a therapeutic composition.

12 Claims, No Drawings

METHOD FOR THE TREATMENT OF BRADYPHRENIA IN PARKINSON'S DISEASE PATIENTS

This application is a divisional of Ser. No. 07/954,258, filed Sep. 30, 1992, now U.S. Pat. No. 5,352,688, which is a continuation-in-part of prior application, Ser. No. 07/743,254, filed Aug. 9, 1991, now U.S. Pat. No. 5,177,081, which is a divisional of application Ser. No. 655,759, filed Feb. 14, 1991, now U.S. Pat. No. 5,070,101. The disclosure of U.S. Pat. No. 5,070,101 is incorporated herein by reference.

BACKGROUND OF THE INVENTION

This application relates to a method and composition for use in the treatment of Parkinson's Disease.

Parkinson's Disease was first described in 1817 by James Parkinson in a paper entitled "An Essay on the Shaking Palsy". Since then, it has become increasingly clear that Parkinson's Disease involves a complex cluster of symptoms which respond differently to therapeutic treatments.

These symptoms can be classified into two groups: those manifesting themselves as motor dysfunction, and those which can be characterized as neuropsychiatric disorders or symptoms. In the latter group there are three recognized components, (1) apathy-amotivation; (2) depression and (3) dementia.

The motor dysfunction symptoms of Parkinson's Disease have been treated in the past using dopamine receptor agonists, monoamine oxidase binding inhibitors, anticholinergics and histamine $H_1$-antagonists, although it is probable that it is the anticholinergic rather than the antihistamine activity of the latter group which is responsible for therapeutic effects. These treatments have little or no benefit with respect to the neuropsychiatric symptoms.

It is an object of the present invention to provide a treatment for the neuropsychiatric symptoms of Parkinson's Disease.

SUMMARY OF THE INVENTION

In accordance with the present invention, neuropsychiatric symptoms of Parkinson's Disease and particularly the symptoms of apathy-amotivation and mental slowing can be ameliorated by treating a patient suffering from Parkinson's Disease with a histamine $H_2$-antagonist that passes the blood brain barrier. Suitable $H_2$-antagonists include famotidine and ranitidine.

The $H_2$-antagonists may be co-administered with other compounds which are known to be useful in the treatment of Parkinson's Disease, and in one aspect of the invention can be formulated with such other compounds into a therapeutic composition.

DETAILED DESCRIPTION OF THE INVENTION

The claimed invention relates to treatment of the apathy-amotivation and mental slowing observed in Parkinson's patients. These symptoms have been referred to as bradyphrenia, psychic akinesia or subcortical dementia. The term "bradyphrenia" will be used in the specification and claims hereof to refer to these symptoms.

Bradyphrenia is similar in its manifestation to the negative symptoms of schizophrenia and the pathophysiology may be related, although there is no indication that the etiology of these symptoms are the same. Nevertheless, these symptoms respond to the same therapy which I found to be effective for treating schizophrenia. Thus, bradyphrenia is treated in accordance with the invention by administering a histamine $H_2$-antagonist that passes the blood-brain barrier to the patient. Suitable histamine $H_2$-antagonists include famotidine, ranitidine, cimetidine, nizatidine, omeprazole, tiotidine and aminofurazan compounds.

The preferred mode of administration is oral administration. Preparations for oral administration can be formulated in various forms (e.g. liquid, tablets, capsules) and may include appropriate excipients, flavorants, colorants and other carrier materials. Other modes of administration, including intraperitoneal, intravenous and intramuscular administration can be employed, however, particularly if the patient is uncooperative.

In addition to the $H_2$-antagonist and appropriate carrier materials, the pharmaceutical preparation may include one or more therapeutic agents effective against symptoms of Parkinson's Disease other than bradyphrenia. Such materials include levodopa, carbidopa histamine $H_1$-antagonists (e.g. diphenhydramine), dopamine receptor agonists (e.g. apomorphines and ergotamines), anticholinergics (e.g. trihexyphenidyl), monoamine oxidase binding inhibitors (e.g. deprenyl), and compounds with combined actions (orphenadrine, chlorphenoxamine and benztropine).

Histamine $H_2$-antagonists are administered in amounts sufficient to ameliorate the symptoms of bradyphrenia. For example, $H_2$-antagonists are suitably administered in amounts of 20–600 mg/day, although the upper limit is imposed by a concern over side effects rather than a loss of efficacy. Preferably, the $H_2$-antagonist is administered in an amount of from 80–160 mg/day. Pharmaceutical compositions in accordance with the invention are prepared to deliver the effective amount of $H_2$-antagonist in view of the anticipated frequency of treatment.

While not intending to be bound to a particular theory, the efficacy of histamine $H_2$-antagonists in the treatment of neuropsychiatric symptoms of Parkinson's disease is believed to result from a reversal of the effects of elevated histamine levels on the $H_2$ receptors of the brain to increase the level of arousal and motivated behavior. This theory is consistent with the observation of elevated blood histamine levels in untreated Parkinson's patients. Coelho et al., Molecular & Chemical Neuropathology 14, 77–85 (1991). It is also consistent with the observation that $H_2$-receptors in the brain are predominantly localized in the same portions of the brain, i.e., the caudate putamen and the globus pallidus, that are implicated in the pathophysiology of Parkinson's disease, Martinez-Mir et al., Brain Research 526, 322–327 (1990); and the hypothesis that hyperactive histamine neurons resulting from a dopamine deficiency may be involved in Parkinson's disease. Garbarg et al., The Lancet 1, 74–75 (1983). Nevertheless, no association between histamine and the neuropsychiatric symptoms of Parkinson's Disease has been suggested prior to this invention.

I claim:

1. A method for treating the symptoms of bradyphrenia in a patient suffering from Parkinson's Disease comprising administering to the patient a histamine $H_2$-antagonist that crosses the blood brain barrier in an amount effective to ameliorate the symptoms of bradyphrenia.

2. A method according to claim 1, wherein the histamine $H_2$-antagonist is administered in an amount of from 20 to 600 mg/day.

3. A method according to claim 2 wherein the histamine $H_2$-antagonist is administered in an amount of from 80 to 160 mg/day.

4. A method according to claim 1, wherein the histamine $H_2$-antagonist is famotidine.

5. A method according to claim 4, wherein the histamine $H_2$-antagonist is administered in an amount of from 20 to 600 mg/day.

6. A method according to claim 5 wherein the histamine $H_2$-antagonist is administered in an amount of from 80 to 160 mg/day.

7. A method according to claim 1, wherein the histamine $H_2$-antagonist is ranitidine.

8. A method according to claim 1, further comprising the step of co-administering at least one additional therapeutic agent effective against symptoms of Parkinson's disease other than bradyphrenia.

9. A method according to claim 8, wherein the additional therapeutic agent is a dopamine receptor agonist.

10. A method according to claim 8, wherein the additional therapeutic agent is a histamine $H_1$-antagonist.

11. A method according to claim 8, wherein the histamine $H_2$-antagonist is famotidine.

12. A method according to claim 8, wherein the histamine $H_2$-antagonist is ranitidine.

* * * * *

UNITED STATES PATENT AND TRADEMARK OFFICE
CERTIFICATE OF CORRECTION

PATENT NO. : 5,547,969
DATED : Aug. 20, 1996
INVENTOR(S) : Ram Kaminski

It is certified that error appears in the above-indentified patent and that said Letters Patent is hereby corrected as shown below:

On title page, Item [*] Notice, 3rd line, "5,5,352,688" should read --5,352,688--;

Col. 2, line 20, "carbidopa histamine" should read --carbidopa, histamine--.

Signed and Sealed this

Fourth Day of February, 199

Attest:

BRUCE LEHMAN

Attesting Officer  Commissioner of Patents and Trademarks